(12) United States Patent
Ly et al.

(10) Patent No.: US 11,931,056 B2
(45) Date of Patent: Mar. 19, 2024

(54) RETRACTABLE ELEVATOR INSTRUMENT SHAVER BLADE WITH FLUSH/LAVAGE FEATURES

(71) Applicant: GYRUS ACMI, INC., Southborough, MA (US)

(72) Inventors: Canh S. Ly, Cordova, TN (US); Joey Magno, Cordova, TN (US)

(73) Assignee: Gyrus ACMI, Inc., Westborough, MA (US)

( * ) Notice: Subject to any disclaimer, the term of this patent is extended or adjusted under 35 U.S.C. 154(b) by 611 days.

(21) Appl. No.: 17/017,936

(22) Filed: Sep. 11, 2020

(65) Prior Publication Data

US 2021/0100571 A1     Apr. 8, 2021

Related U.S. Application Data

(60) Provisional application No. 62/969,293, filed on Feb. 3, 2020, provisional application No. 62/910,147, filed on Oct. 3, 2019.

(51) Int. Cl.
   *A61B 17/32*     (2006.01)
   *A61B 17/24*     (2006.01)
   *A61M 3/02*      (2006.01)

(52) U.S. Cl.
   CPC ...... *A61B 17/24* (2013.01); *A61B 17/320016* (2013.01); *A61M 3/0279* (2013.01); *A61B 2217/007* (2013.01); *A61M 2210/0681* (2013.01)

(58) Field of Classification Search
   CPC . A61B 17/24; A61B 17/32; A61B 17/320016; A61B 17/32002; A61B 2017/320004; A61B 2017/320008; A61B 2017/320024; A61B 2017/320056; A61B 2217/007
   See application file for complete search history.

(56) References Cited

U.S. PATENT DOCUMENTS

| | | | |
|---|---|---|---|
| 6,183,433 B1 | 2/2001 | Bays | |
| 6,464,711 B1 * | 10/2002 | Emans | A61B 17/32002 606/167 |
| 8,313,489 B2 | 11/2012 | Adams et al. | |
| 2005/0054972 A1 * | 3/2005 | Adams | A61B 17/32002 606/180 |
| 2007/0255289 A1 * | 11/2007 | Nakao | A61B 17/32 606/205 |

* cited by examiner

*Primary Examiner* — Diane D Yabut
*Assistant Examiner* — Christian D Knauss
(74) *Attorney, Agent, or Firm* — Schwegman Lundberg Woessner, P.A.

(57) ABSTRACT

A device having a hub assembly and a lever coupled with the hub assembly is provided. The device includes a sheath coupled with the lever and extending from the hub assembly. The sheath has a surgical elevator with a surgical elevator edge along with a hypotube having an access hole. The device has a shaver blade assembly with an outer shaft having an outer blade and an inner blade within the outer blade. The outer shaft has a stop and an access hole near the outer and inner blades. The sheath partially surrounds the outer shaft and the lever moves between a first position and a second position. In the first position, the surgical elevator edge abuts the outer shaft stop and the outer shaft access hole aligns with the hypotube access hole. In the second position, the surgical elevator edge is spaced apart from the outer shaft stop.

20 Claims, 12 Drawing Sheets

RETRACTABLE ELEVATOR INSTRUMENT SHAVER BLADE WITH FLUSH/LAVAGE FEATURES

CROSS-REFERENCE TO RELATED APPLICATION

This application claims priority to U.S. Provisional Patent Application No. 62/910,147, filed on Oct. 3, 2019 and U.S. Provisional Patent Application No. 62/969,293, filed on Feb. 3, 2020; the contents of which are incorporated herein in their entireties.

TECHNICAL FIELD

This document pertains generally, but not by way of limitation, to surgical instruments and methods that include surgical tooling that can be used for endoscopic surgical procedures. More specifically, but not by way of limitation, the present application relates to a multifunctional surgical instrument.

BACKGROUND

Blockages in sinus cavities of patients can cause a number of issues with patients, such as chronic rhinosinusitis, which can lead to difficulty breathing through the nose, chronic sinofacial pain or headaches, post nasal drip, or a reduced sense of smell and taste. Typically, these blockages can be caused by various anatomical factors, such as a deviated septum or nasal polyps. Endoscopic procedures, such as functional endoscopic sinus surgery (FESS), is used to remove blockages from the sinus cavities. In addition to treating chronic rhinosinusitis, FESS can be used to treat some forms of cancer along with the decompression of eye sockets caused by thyroid eye disease.

During FESS, a surgeon passes two narrow tubes into the sinus cavity of a patient. One of the narrow tubes includes an endoscope that allows the surgeon to view a problem site within the sinus cavity. Using the other narrow tube, the surgeon may pass small surgical instruments to the problem site of the sinus cavity. One of the surgical instruments used during FESS may be an ENT elevator, such as a Freer ENT elevator. A Freer ENT elevator is used to manually resect tissue causing a sinus cavity blockage from the sinus cavity. A Freer ENT elevator may be used for precision cutting within the sinus cavity.

One issue that arises during FESS relates to the surgeon having to switch between instruments during irrigation while using the Freer ENT elevator. To further illustrate, the surgeon can have to remove the Freer ENT elevator in order to perform irrigation during FESS. Furthermore, while a Freer ENT elevator is useful for precision removal of tissue from the sinus cavity, a Freer ENT elevator is not practical for removing large amounts of tissue. More specifically, a Freer ENT allows for manual resection of tissue. If a great amount of tissue resection is required, using the Freer ENT would increase the time associated with removing the tissue as opposed to using an automated device. Therefore, the surgeon must remove the Freer ENT elevator from the narrow tube and insert a different instrument that is more suitable for the removal of large amounts of tissue.

Accordingly, what is needed is an instrument that is capable of being used during an endoscopic procedure, such as FESS, where the instrument is capable of precision removal of tissue while at the same time is capable of removing large amounts of tissue. Furthermore, what is needed is an instrument that is capable of providing irrigation to the surgical site during tissue removal.

SUMMARY

Examples of the present disclosure relate to an endoscopic sinus surgery device having a shaver blade assembly and an outer sheath disposed about the shaver blade assembly along with a hub assembly. In an example, the shaver blade assembly can include an outer shaft with an outer blade disposed at a distal end and an inner blade disposed inside both the outer shaft and the outer blade. In an example, the outer sheath can be disposed about the outer shaft and can be configured to move in an axial direction relative to the outer shaft. According to an example, the outer sheath can include a surgical elevator at a distal end that can be configured to mate with a bottom surface of the shaver blade assembly in a retracted position. The hub assembly can have a lever that couples with the hub assembly, the outer sheath or both. For example, the lever may be coupled to the hub assembly via a set of upper pins and to the outer sheath via a set of lower pins. In some implementations, the lever can be activated via axial movement. For example, the level may be moved in a proximal direction in order to extend the outer sheath in an axial direction relative to the shaver blade such that the shaver blade assembly is in an extended position. In the extended position, the surgical elevator may be spaced apart from the shaver blade. Furthermore, the lever can be activated in a distal direction in order to retract the outer sheath in the axial direction relative to the shaver blade such that the surgical elevator mates with the bottom surface of the shaver blade.

In an example of the present disclosure, the outer sheath can include a multifunctional hypotube having a hypotube access hole. In an example, the shaver blade assembly can include a shaver blade assembly access hole that aligns with the hypotube access hole when the shaver blade assembly is in the retracted position. In this configuration, the hypotube access hole may be configured to provide irrigation to the shaver blade assembly during operation of the shaver blade assembly. Moreover, when the shaver blade assembly is in the extended position, as irrigant flows through the hypotube access hole, the irrigant creates a lavage effect.

DETAILED DESCRIPTION

Examples of the present disclosure relate to an endoscopic sinus surgery device having a shaver blade assembly and an outer sheath disposed about the shaver blade assembly along with a hub assembly. In an example, the shaver blade assembly can include an outer shaft with an outer blade disposed at a distal end and an inner blade disposed inside both the outer shaft and the outer blade. In an example, the outer sheath can be disposed about the outer shaft and can be configured to move in an axial direction relative to the outer shaft. According to an example, the outer sheath can include a surgical elevator at a distal end that can be configured to mate with a bottom surface of the shaver blade assembly in a retracted position. The hub assembly can have a lever that couples with both the hub assembly and the outer sheath. For example, the level may be coupled to the hub assembly via a set of upper pins and to the outer sheath via a set of lower pins. In an example, the lever can be activated in a proximal direction in order to extend the outer sheath in an axial direction relative to the shaver blade such that the shaver blade assembly can be in an extended position. In the extended position, the surgical elevator can be spaced apart from the shaver blade, as will be further discussed further below with respect to FIG. 3. Furthermore, the lever can be activated in a distal direction in order to retract the outer sheath in the axial direction relative to the shaver blade such that the surgical elevator mates with the bottom surface of the shaver blade.

In an example of the present disclosure, the outer sheath can include a multifunctional hypotube having a hypotube access hole. In an example, the shaver blade assembly can include a shaver blade assembly access hole that aligns with the hypotube access hole when the instrument is in the retracted position. In this configuration, the hypotube access hole may provide irrigation to the shaver blade assembly during operation of the instrument. Moreover, when the instrument is in the extended position, as irrigant flows through the hypotube access hole, the irrigant creates a lavage effect.

Figure 1:
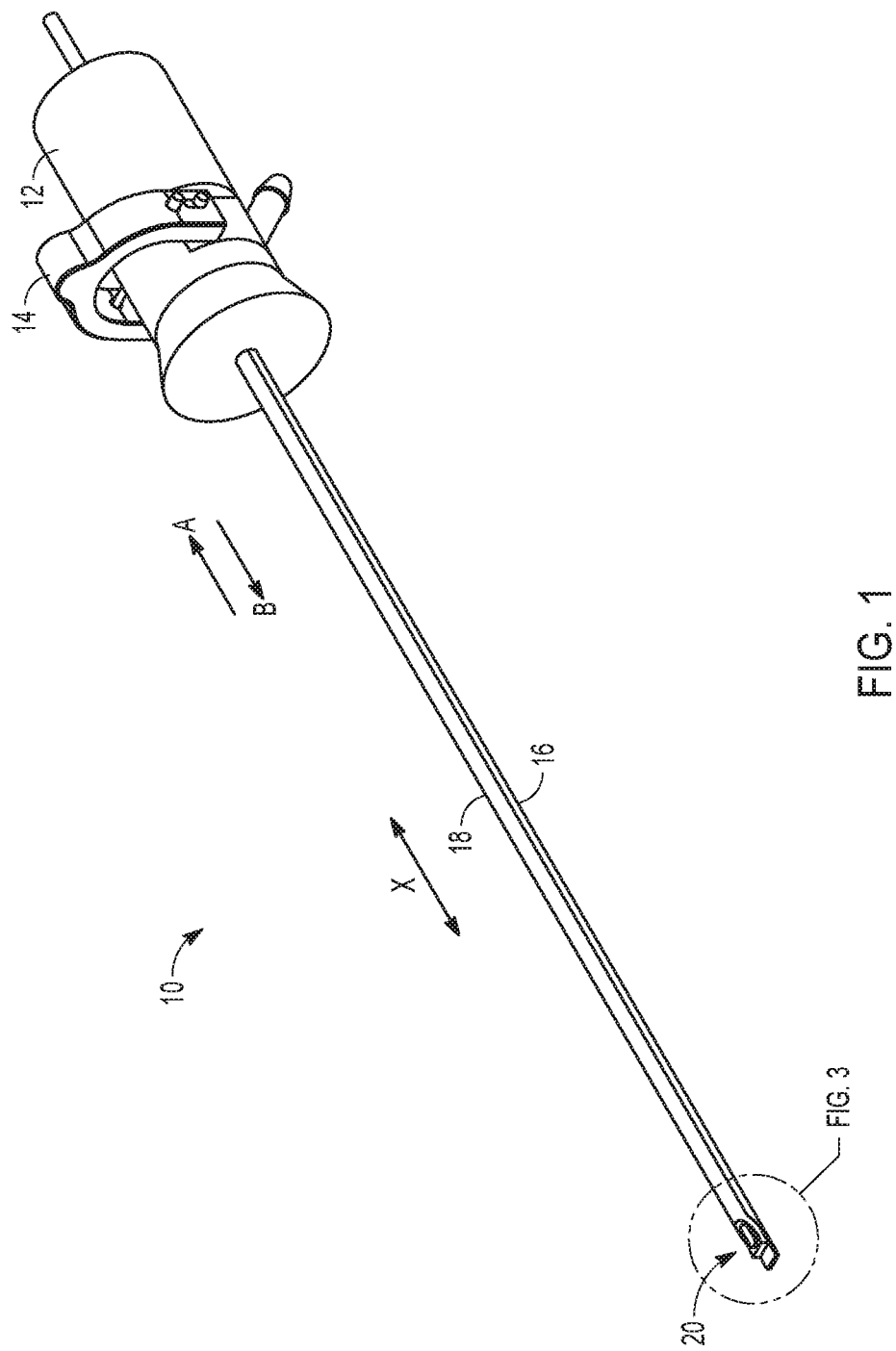
FIGS. 1 and 2 illustrate perspective views of an endoscopic sinus surgery device in accordance with examples of the present disclosure.
Figure 2:
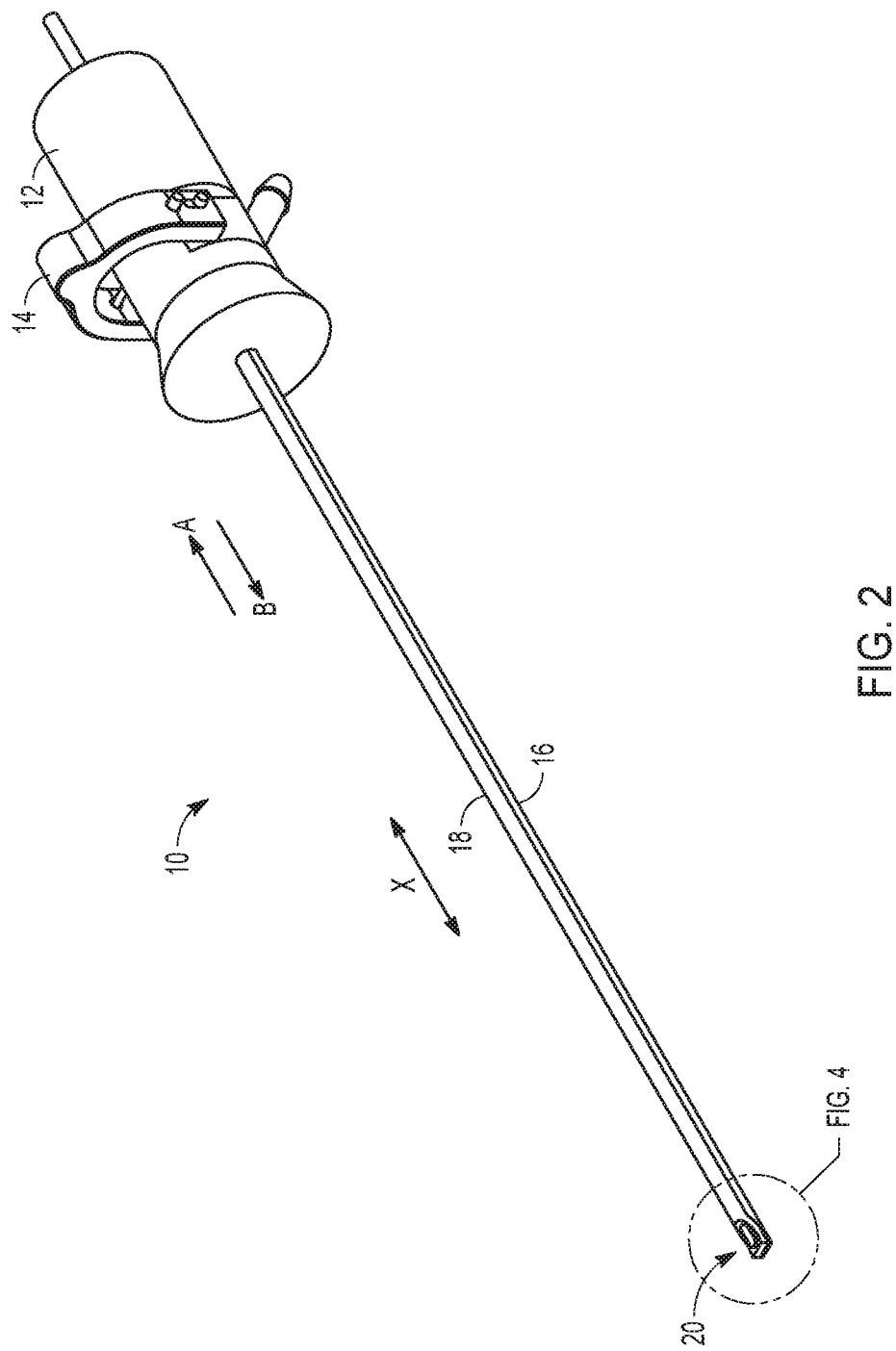

FIG. 1 shows a perspective view of an endoscopic sinus surgery device 10 in accordance with examples of the present disclosure. In the example shown in FIG. 1, the endoscopic sinus surgery device 10 includes a hub assembly 12 and a lever 14. In some implementations, the lever 14 may be used to control how resection is performed during use of the endoscopic sinus surgery device 10. The endoscopic sinus surgery device 10 can also include an outer sheath 16 disposed about an outer shaft 18 of a shaver blade assembly 20. In an example, the outer sheath 16 can move in an axial direction X relative to the outer shaft 18 in order to provide different functionalities for the endoscopic sinus surgery device 10. For example, the lever 14 can be activated in a direction A along the axial axis X in order to lock the endoscopic sinus surgery device 10 in an extended position, as shown with reference to FIG. 1. Moreover, the lever 14 can be activated in a direction B in order to lock the endoscopic sinus surgery device 10 in a retracted position, as shown with reference to FIG. 2. In an embodiment, the position of the endoscopic sinus surgery device 10 can dictate the functionality of the endoscopic sinus surgery device 10. In particular, as will be discussed in greater detail with reference to FIG. 3, when the endoscopic sinus surgery device 10 is in the position shown in FIG. 1, i.e., in the extended position, a tip of the endoscopic sinus surgery device 10 can extend away from a distal end of the endoscopic sinus surgery device 10 such that the endoscopic sinus surgery device 10 may be used for manual tissue resection. In the position shown with regards to FIG. 2, i.e., the retracted position, as will be detailed with reference to FIG. 4, the tip of the endoscopic sinus surgery device 10 abuts the distal end of the endoscopic sinus surgery device 10 such that the shaver blade assembly 20 may be used for tissue resection.

In the extended position, the endoscopic surgery device 10 can be used for manual resection. An example of the endoscopic surgery device 10 being in the extended position is shown with reference to FIG. 3. Here, the outer sheath 16 can include a surgical elevator 22 disposed at a distal end thereof. In an example, the surgical elevator 22 can include a surgical elevator edge 24 extending from an edge of the surgical elevator 22, as shown with reference to FIG. 3. In some examples, the surgical elevator edge 24 can be a sharpened edge, such that the surgical elevator 22 functions similar to a Freer elevator. In particular, when the endoscopic sinus surgery device 10 is in the extended position, as shown with reference to FIG. 3, a surgeon can use the surgical elevator 22 in conjunction with the surgical elevator edge 24 to manually resect tissue. In the extended position, the surgical elevator 22 is spaced apart from the outer shaft 18, as shown with respect to FIG. 3. In other words, the surgical elevator 22 does not abut the outer shaft 18 such that there is a gap between the surgical elevator 22 and the outer shaft 18 in order to allow manual resection with the surgical elevator edge 24. For example, during endoscopic sinus surgery, such as a nasal polypectomy procedure, a surgeon can use the lever 14 to place the endoscopic sinus surgery device 10 in the extended position and use the surgical elevator edge 24 to manually resect tissue from nasal cavities, paranasal sinuses, or the like, when precise tissue removal is preferred. In addition to the surgical elevator 22, the outer sheath 16 can include a hypotube 26 having an hypotube access hole 28. As will be discussed further on, in some implementations, the hypotube 26 and the hypotube access hole 28 are configured to provide irrigation and a lavage effect when the surgical elevator 22 is employed during use of the endoscopic sinus surgery device 10.

Figure 3:
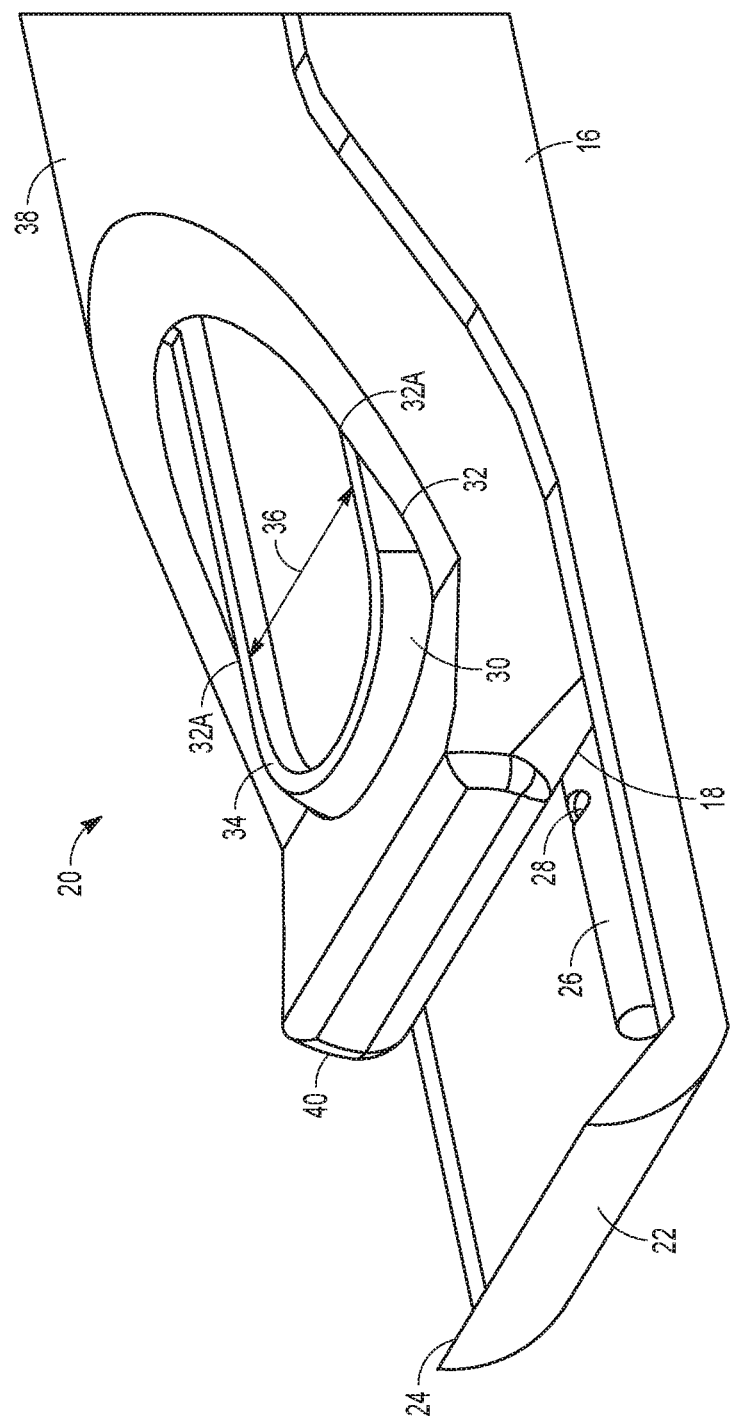
FIG. 3 illustrates an endoscopic sinus surgery device in an extended position in accordance with examples of the present disclosure.
Figure 4:
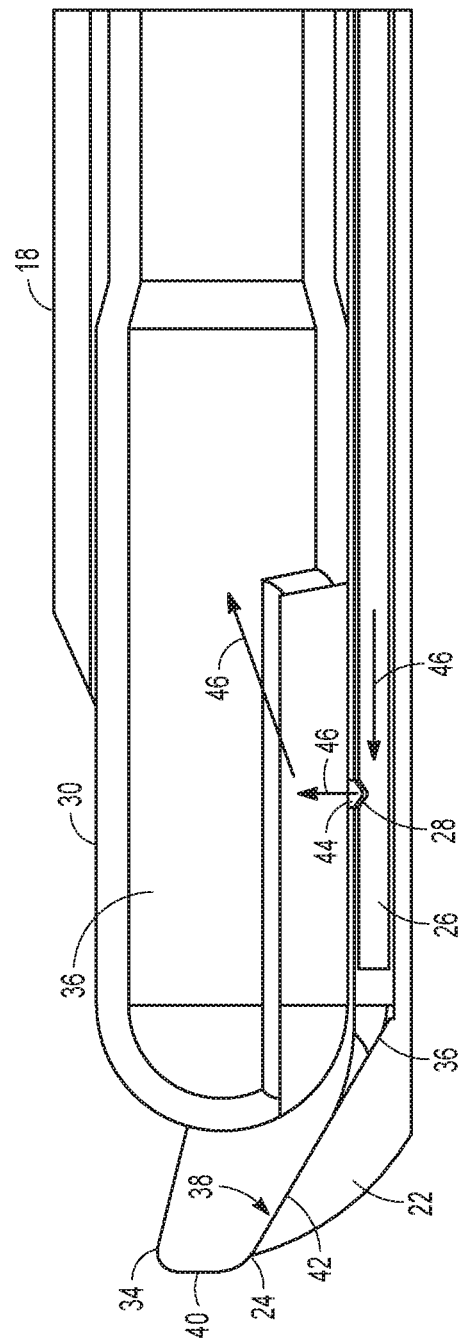
FIG. 4 illustrates an endoscopic sinus surgery device in a retracted position in accordance with examples of the present disclosure.

Still making reference to FIG. 3, as noted above, the endoscopic sinus surgery device 10 can include the shaver blade assembly 20. In accordance with an example of the present disclosure, the shaver blade assembly 20 can include an inner blade 30 disposed within the outer shaft 18 along with an outer blade 32 disposed about the inner blade 30. In an embodiment, the inner blade 30 can be partially disposed within the outer blade 32. The inner blade 30 can include an inner blade edge 34, which defines an inner blade window 36. Moreover, the inner blade edge 34, in conjunction with the outer blade 32 cooperate with each other to create a resection surface 32A, which can be used for resection during use of the endoscopic sinus surgery device 10. More specifically, in an embodiment, the inner blade assembly 30 can rotate relative to the outer blade 32. As the inner blade 30 rotates, the inner blade edge 34 can move relative to the outer blade 32 and, at 32A, a resection surface is created. It should be noted that while the resection surface 32A is shown at a particular point, the resection surface 32A will move along the outer blade 32 as the inner blade 30 rotates. While the inner blade 30 is shown as a planar blade for ease of discussion, the inner blade 30 can be any type of blade that can be used for resection, such as a straight sinus blade, a curved sinus blade, a turbinate blade, or the like. Moreover, while the outer blade 32 is shown as being planar for ease of discussion, in accordance with examples, the outer blade 32 can have a curved sinus blade configuration.

In some implementations, the shaver blade assembly 20 is configured to abut the surgical elevator 22 when the endoscopic sinus surgery device 10 is in a retracted position. More specifically, the outer shaft 18 of the shaver blade assembly 20 may include an outer shaft stop 38 at a distal end 40 of the outer shaft 18. As may be seen with reference to FIG. 4, when the endoscopic sinus surgery device 10 is in the retracted position, a surgical elevator surface 42 of the surgical elevator 22 abuts the outer shaft stop 38 of the outer shaft 18. In an embodiment, the stop 38 can function as a surface against which the surgical elevator 22 rests when the endoscopic sinus surgery device 10 is in the retracted position. As noted above, the outer sheath 16 may include the optional hypotube 26 that can have the hypotube access hole 28. In an example, the outer shaft 18 can include an outer shaft access hole 44 in a bottom surface of the outer shaft 18, which, when the endoscopic sinus surgery device 10 is in the retracted position, aligns with the hypotube access hole 28. Moreover, as may be seen with reference to FIG. 4, the surgical elevator 22 can be completely below the distal end 40 of the outer shaft 18. Thus, when the shaver blade assembly 20 is used for tissue resection, the surgical elevator 22 does not interfere with tissue resection, i.e., the surgical elevator 22 does not inadvertently resect tissue.

When the shaver blade assembly 20 is used for tissue resection, the inner blade 30 may axially rotate within the outer shaft 18 and the outer blade 32. As the inner blade 30 rotates the outer blade 32 and the inner blade edge 34 cooperate with one another to resect tissue when the shaver blade assembly 20 is activated. To further illustrate, while the inner blade 30 rotates within the outer shaft 18 and the outer blade 32, the outer blade 32 remains stationary such that tissue, which comes into contact with both the rotating inner blade 30 and the stationary outer blade 32, is resected and captured by the inner blade window 36. Furthermore, during tissue resection with the shaver blade assembly 20, while the endoscopic sinus surgery device 10 is in the retracted position, the surgical elevator surface 42 abuts the outer shaft stop 38 such that the surgical elevator 22 can be positioned lower than the shaver blade assembly 20. Therefore, the surgical elevator edge 24 does not interfere with tissue resection when the shaver blade assembly 20 is in use. Still referring to FIG. 4, when the shaver blade assembly is used to resect tissue, the shaver blade assembly 20 is configured to provide the irrigant 46 via the hypotube 26 and the access holes 28 and 44 where the irrigant 46 can be provided to the hypotube 26 from the hub assembly 12, as shown with reference to FIG. 5.

Figure 5:
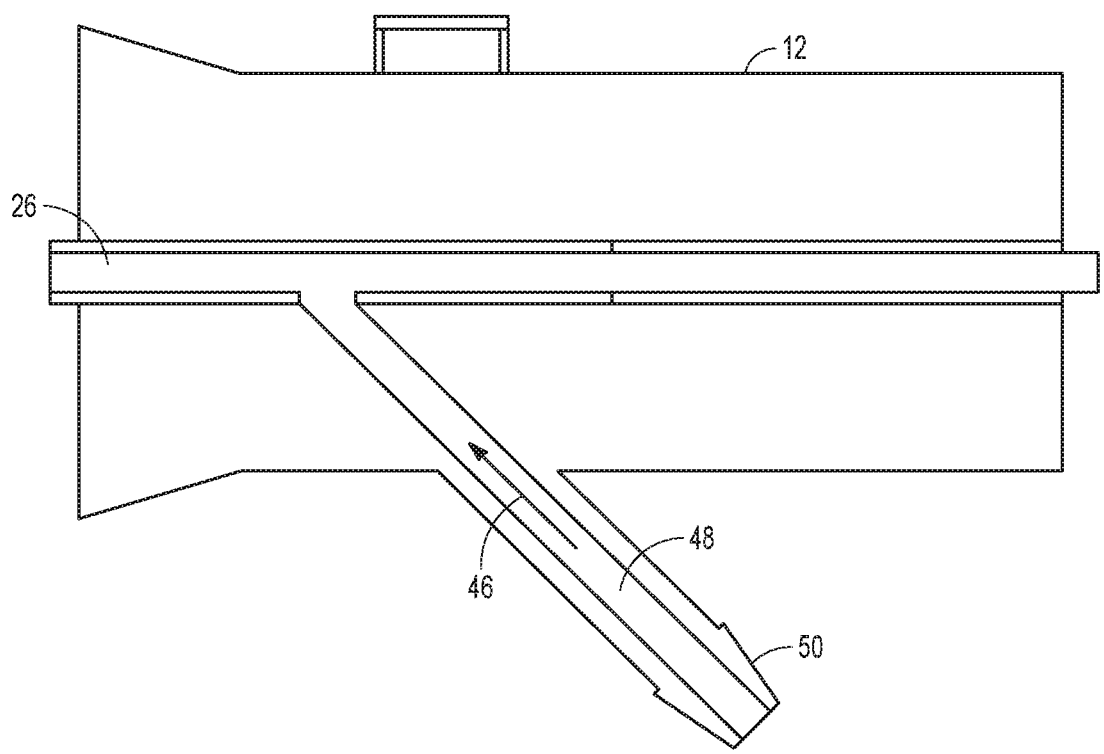
FIG. 5 shows a cross-sectional view of hub assembly of an endoscopic sinus surgery device, in accordance with examples of the present disclosure.

Now making reference to FIG. 5, a cross-sectional view of the hub assembly 12 is shown, in accordance with examples of the present disclosure. In an example, the hub assembly 12 can include a pathway 48 in open fluid communication with the hypotube 26. In addition, the hub assembly 12 can also include a pathway barb 50 disposed at a distal end of the pathway 48, where the pathway barb facilitates the connection of an irrigant source (not shown) such as an IV bag or a pouch, that provides the irrigant 46 to the hub assembly 12. Additionally, examples of irrigant that may be used include any mixture of Sodium Chloride (saline). To further illustrate, a 0.9% Sodium Chloride solution may be used in an embodiment. Referring back to FIG. 4, during use of the shaver blade assembly 20, the irrigant 46 provided by the hub assembly 12 travels from the hypotube 26 and into the inner blade window 36 of the inner blade 30. As one skilled in the art will appreciate, the irrigant 46 may increase resection efficiency of the shaver blade assembly 20. Furthermore, as one skilled in the art will appreciate, the irrigant 46 may cool the shaver blade assembly 20 when the shaver blade assembly 20 is used for tissue resection. In the retracted position, the lavage function can be initiated to assist in clearing any clogs downstream of the shaver blade.

Figure 6:
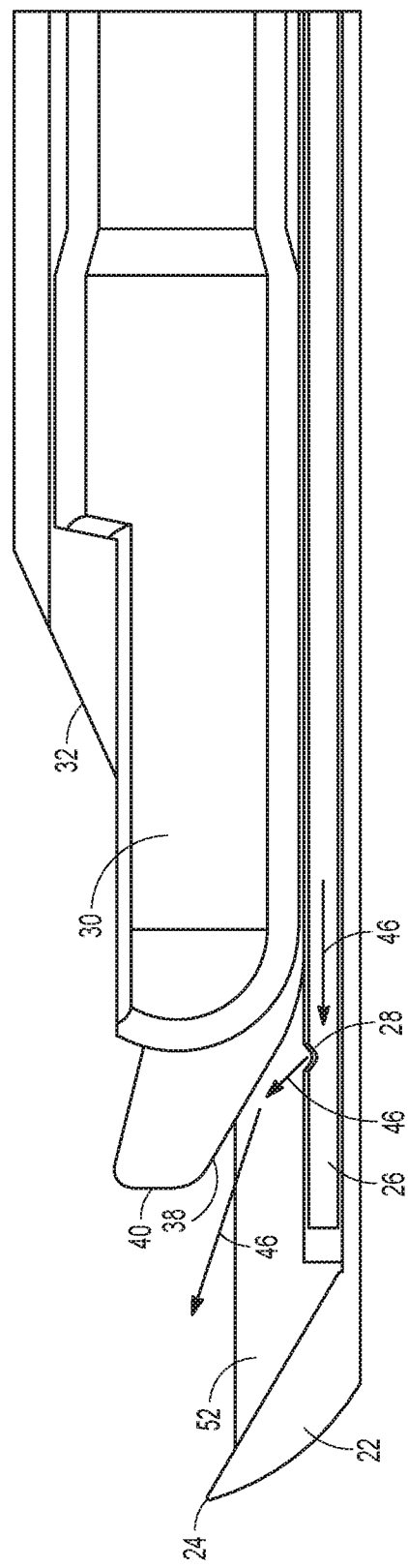
FIGS. 6 and 7 illustrate an endoscopic sinus surgery device in an extended position in accordance with examples of the present disclosure.
Figure 7:
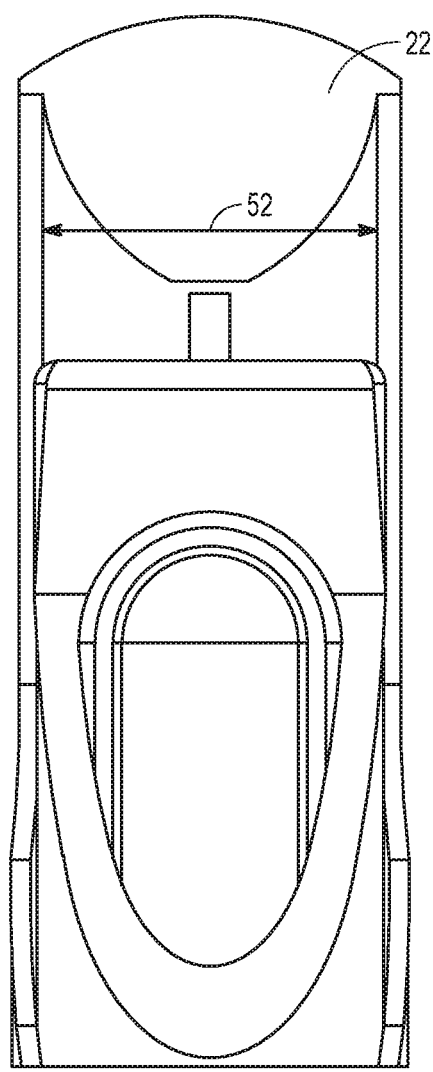

In addition, the irrigant 46 can be provided when the surgical elevator 22 is used for tissue resection. In particular, as shown with reference to FIGS. 6 and 7, the surgical elevator 22 includes a surgical elevator window 52. In an example, the surgical elevator window 52 can be formed when the surgical elevator 22 is spaced apart from the outer shaft stop 38, i.e., the endoscopic surgery device 10 is an extended position, as shown with reference to FIG. 6. When the surgical elevator 22 is used for tissue resection, the irrigant 46 flows from the hypotube access hole 28 through the surgical elevator window 52 of the surgical elevator 22. In an example, when the irrigant 46 flows through the surgical elevator window 52, a lavage effect can be created, where the irrigant 46 goes into the surgical site and assists with washing out the surgical site. As one skilled in the art will appreciate, the lavage effect created by the flow of irrigant 46 to the surgical site may assist with tissue resection by flushing, clearing or washing away any debris that prevents the surgeon from visualizing and accessing the target tissue. Moreover, as one skilled in the art will appreciate, the lavage effect may also refer to using a pressurized spray to clear external debris. Furthermore, flushing may refer to a low flow clearance of internals.

Figure 8A:
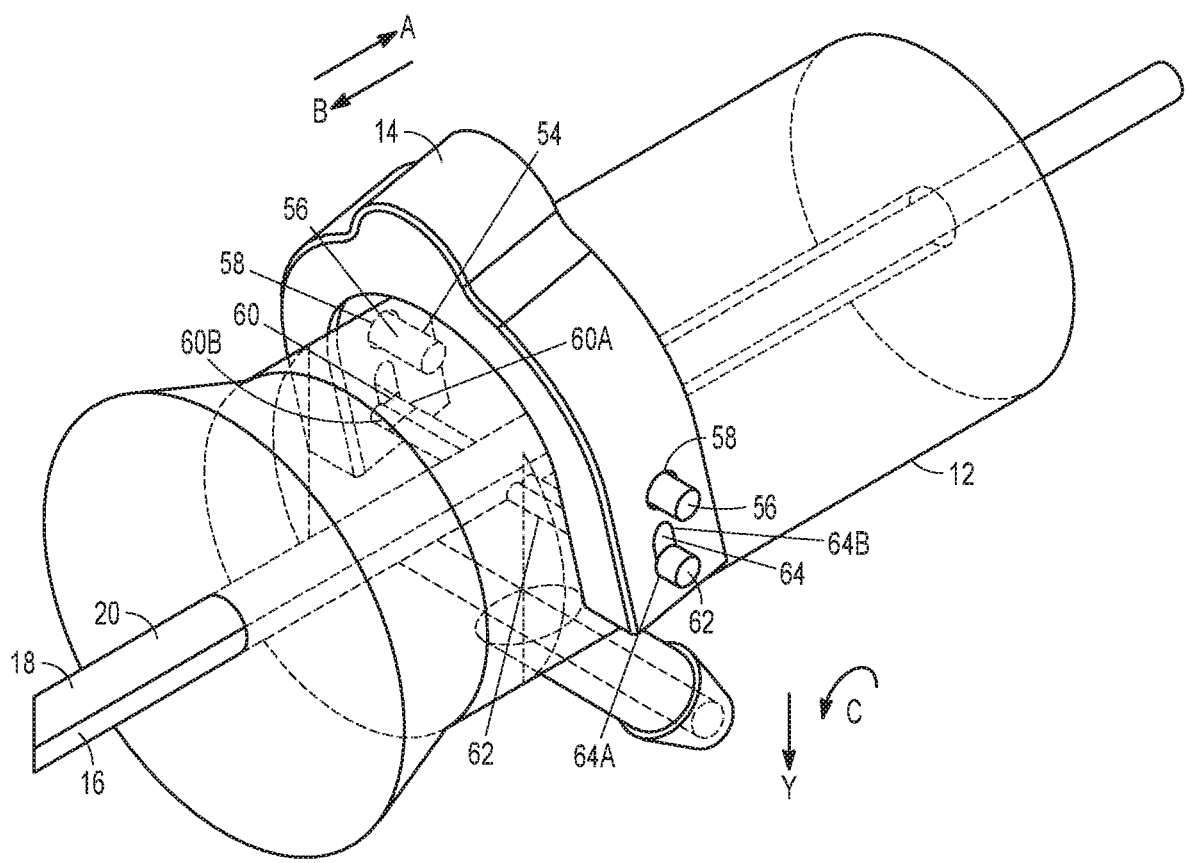
FIGS. 8A and 8B illustrate a position of a lever of an endoscopic sinus surgery device in a retracted position, in accordance with examples of the present disclosure.
Figure 8B:
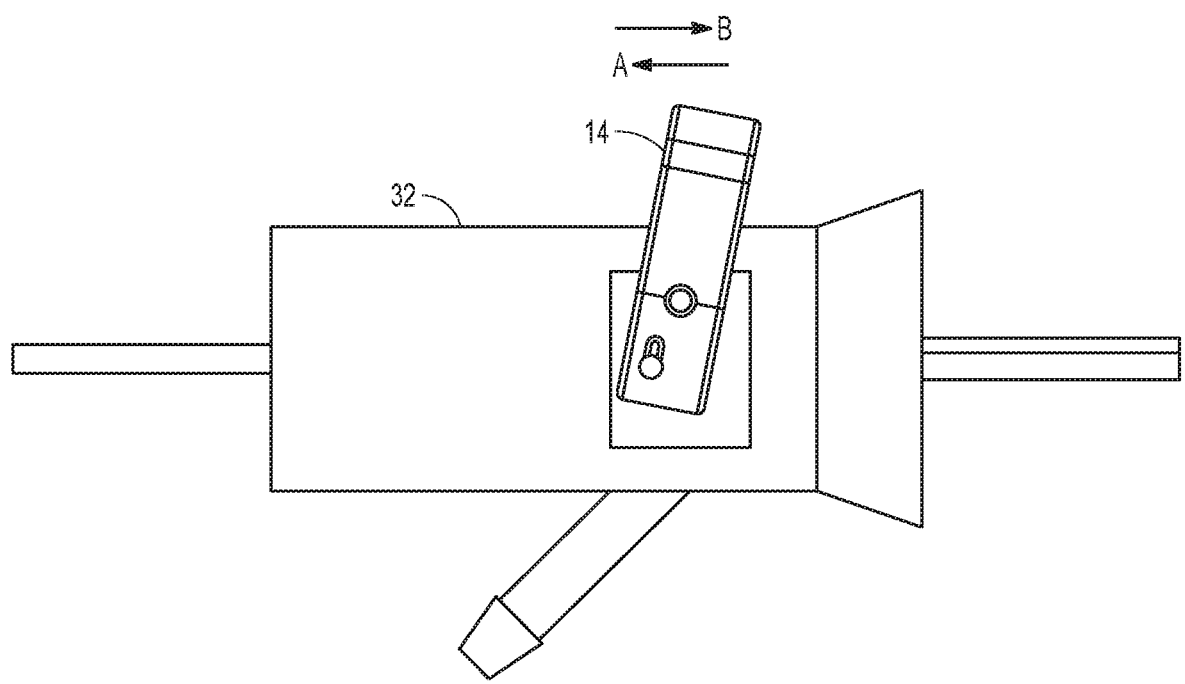

As noted above, the lever 14 can be positioned to lock the endoscopic sinus surgery device 10 in either the extended position or the retracted position. An example of the lever 14 positioned when the endoscopic sinus surgery device 10 is locked in the retracted position is shown with reference to FIGS. 8A and 8B. In an example, the hub assembly 12 can include bores 54 into which upper pins 56 fit. The upper pins 56 can also slide through lever holes 58 of the lever 14 and couple the lever 14 with the hub assembly 12. The hub assembly 12 can also include slots 60 in which lower pins 62 travel. Moreover, the lower pins 62 can pass through lever slots 64 of the lever 14. The lower pins 62 can couple with the outer sheath 16 such that when the lower pins 62 move through the slots 60 and 64, the outer sheath 16 also moves. In accordance with embodiments of the present disclosure, the slots 60 and 64 can have any configuration that facilitates travel of the lower pins 62 therein. For example, the slots 60 and 64 can have a rectangular configuration, an oval configuration, a configuration in the shape of a parallelogram, or the like. As shown with regards to FIGS. 8A and 8B, when the endoscopic sinus surgery device 10 is locked in the retracted position, the lower pin 62 can be disposed at an end 64A of the slot 64 while at the same time can be disposed at an end 60A of the slot 60. In an example, the lever 14 can be in this position when the shaver blade assembly 20 is being used for tissue resection such that the endoscopic surgery device 10 has the configuration shown with reference to FIGS. 2 and 4.

Figure 9A:
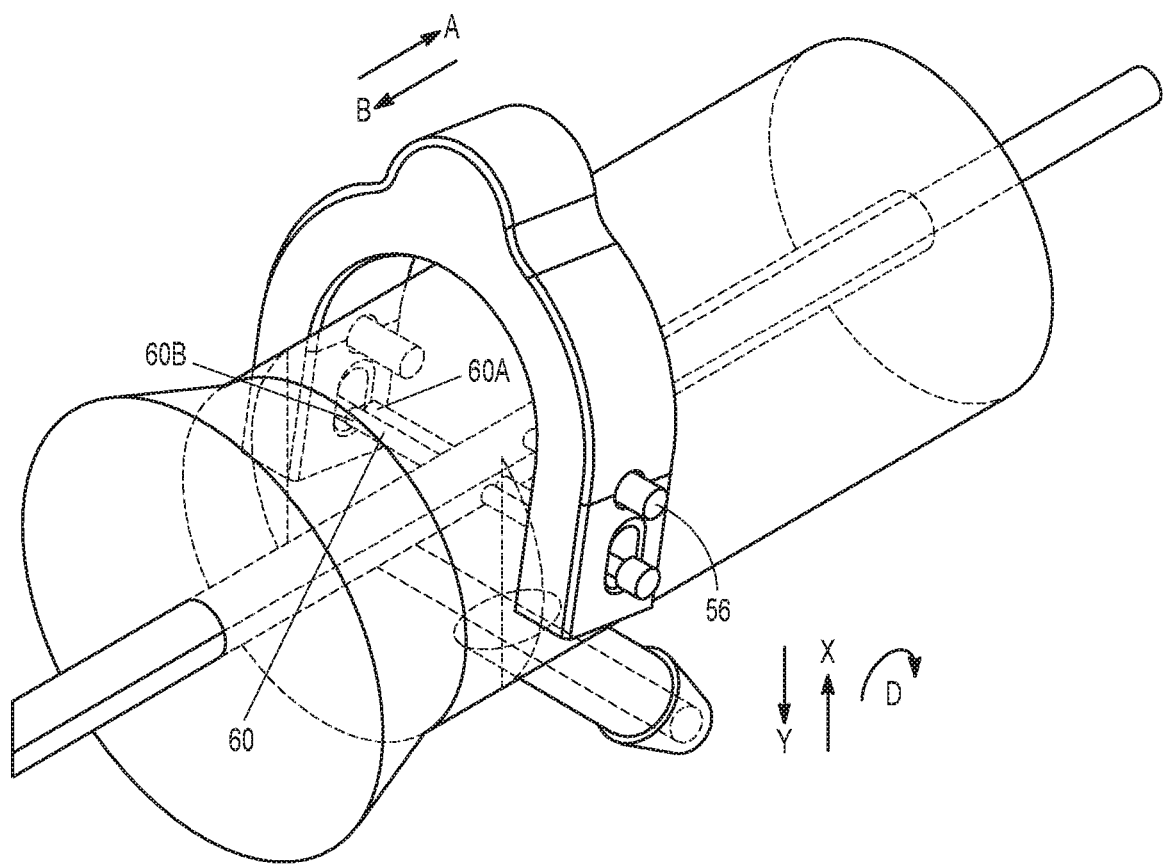
FIGS. 9A and 9B illustrate a position of a lever of an endoscopic sinus surgery device in an extended position, in accordance with examples of the present disclosure.
Figure 9B:
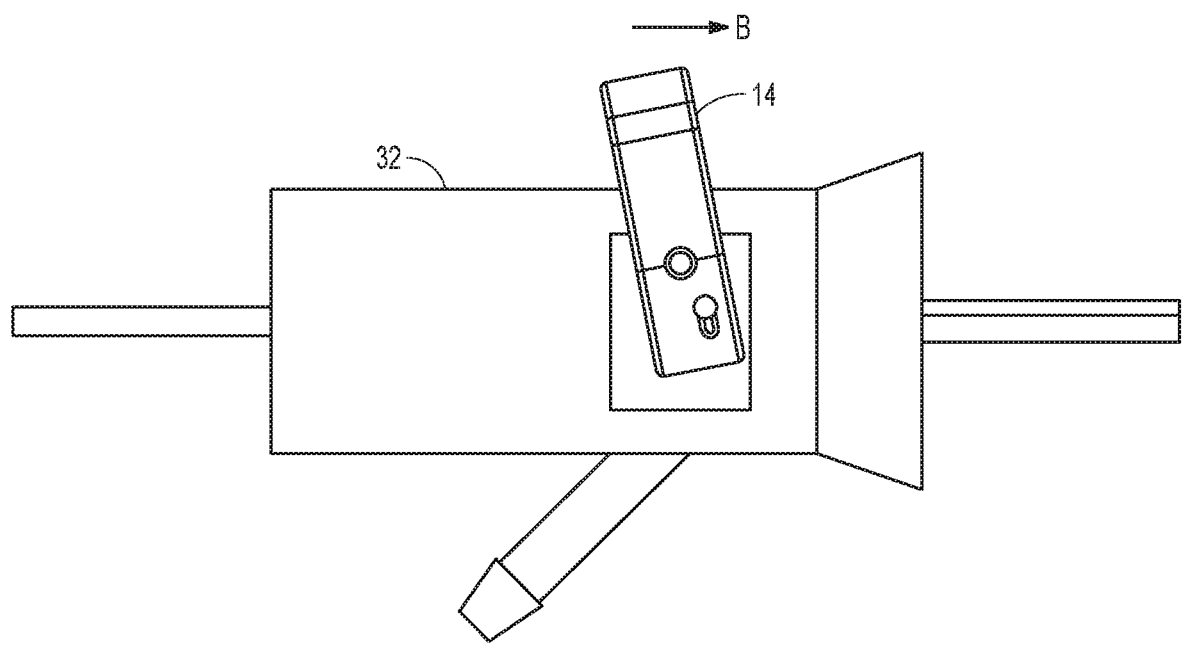

Now making reference to FIGS. 9A and 9B, in an example, when a surgeon desires to implement the surgical elevator 22 for tissue resection, the surgeon can move the lever 14 in the direction A. In an example, as the lever 14 moves in the direction A, the lever 14 can pivot about the upper pins 56 in a direction D. As the lever 14 pivots about the upper pins 56 in a direction D, the lower pin 62 can move through the slot 60 along the direction B. Furthermore, while the lower pins 62 move through the slot 60, the lower pins 62 can move in the lever slot 64 in a direction X. More specifically, when the lever 14 is moved from the fully retracted position shown with reference to FIGS. 8A and 8B, the lower pins 62 can move in the direction X. As noted above, the lower pins 62 can couple with the outer sheath 16. Thus, as the lower pins 62 move in the direction B, towards ends 60B and 64B, the outer sheath can also move in the direction B, causing the surgical elevator 22 to move away from the outer shaft stop 38 of the outer shaft 18. In an example, once the lower pin 62 moves to the ends 60B and 64B thereby locking the endoscopic sinus surgery device 10 in the extended position, as shown with regards to FIGS. 9A and 9B, the window 52 fully opens, as shown with reference to FIGS. 1, 3, 6, and 7.

Figure 10:
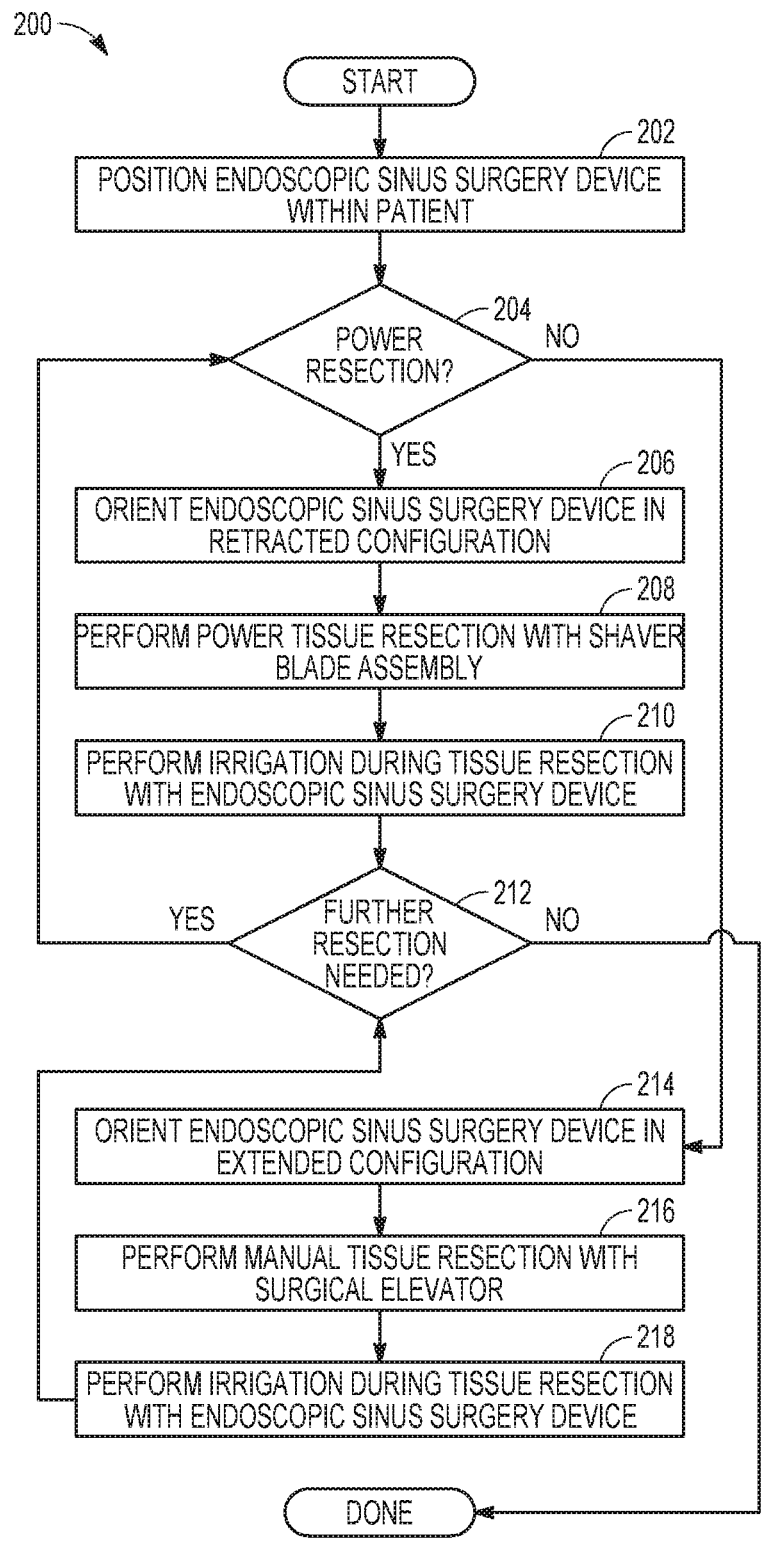
FIG. 10 illustrates a method of using the endoscopic sinus surgery device is shown in accordance with examples of the present disclosure

Now making reference to FIG. 10, a method 200 of using the endoscopic sinus surgery device 10 is shown in accordance with examples of the present disclosure. Initially, the endoscopic sinus surgery device 10 can be positioned within a patient in an operation 202. For example, during a nasal polypectomy procedure, a surgeon can place the endoscopic sinus surgery device 10 within a nasal passage of a patient. After the endoscopic sinus surgery device 10 is positioned within the patient, a determination can be made if power tissue resection will be performed in an operation 204. In accordance with an example, power resection refers to using a powered shaver assembly, such as the shaver blade assembly 20, to perform tissue resection, as opposed to performing tissue resection manually, such as using the surgical elevator 22, to perform tissue resection. If a determination is made to use power tissue resection, an operation 206 can be performed where the endoscopic sinus surgery device can be oriented in a retracted configuration in order to perform power tissue resection with a shaver blade assembly in the operation 208. Moreover, once tissue resection begins in the operation 208, irrigation can also be performed with the endoscopic sinus surgery device in an operation 210 during tissue resection.

Returning to the example, after the endoscopic sinus surgery device 10 is placed in the patient in the operation 202, a determination is made that power tissue resection will be performed in the operation 204. Therefore, if the endoscopic sinus surgery device 10 can be in a position other than the retracted position, the surgeon will move the lever 14 in the direction A such that the lever 14 has the orientation shown in FIGS. 2, 9A, and 9B in the operation 206. Once the endoscopic sinus surgery device 10 and the lever 14 are oriented such that the endoscopic sinus surgery device 10 is in the retracted position, the surgeon can perform power tissue resection with the shaver blade assembly 20 in order to begin removal of polyps during the nasal polypectomy procedure in the operation 208. Moreover, during tissue resection, the hypotube 26 of the endoscopic sinus surgery device 10 can be used to deliver irrigant 46 to the surgical site at which the polyps are being removed during the operation 210. Specifically, as noted above, when the endoscopic sinus surgery device 10 is in the retracted position, the hypotube access hole 28 aligns with the outer shaft access hole 44. Thus, the irrigant 46 can enter into the shaver blade assembly 20 via the inner blade window 36. The irrigant 46 can clean not only the surgical site, in accordance with an example, the irrigant 46 can also clean the shaver blade assembly 20. Moreover, during operation of the endoscopic sinus surgery device 10, in some examples, the irrigant 46 can provide cooling to the inner blade assembly 20.

Returning to FIG. 10 and the method 200, after the operation 210 is performed, an operation 212 can be performed where a determination is made regarding whether or not further tissue resection is needed. If a determination is made that further tissue resection is not needed, the method 200 is done. However, if the method 200 determines that further tissue resection is necessary in the operation 212, the operation 204 is repeated, where a determination is made if power tissue resection is desired. If a determination is made in the operation 204 that power tissue resection is not desired, then an operation 214 is performed where the endoscopic sinus surgery device can be oriented in an extended configuration in order to perform manual resection with the surgical elevator in an operation 216. In addition, once tissue resection begins in the operation 216, irrigation can also be performed with the endoscopic sinus surgery device in an operation 218 during tissue resection.

Returning to the example, after power tissue resection and irrigation are performed in the operations 208 and 210, respectively, the surgeon determines that further tissue resection is needed in the operation 212. Also, the surgeon determines that power tissue resection is not desired in the operation 204. Accordingly, the operation 214 can be performed. In the example, since power tissue resection was just performed, the endoscopic sinus surgery device 10 will be in the retracted position. Therefore, since the endoscopic sinus surgery device 10 is in a position other than the extended position, the surgeon will move the lever 14 in order to move the outer sheath 16 in the direction B such that the lever 14 has the orientation shown in FIGS. 1, 6, 7, 9A, and 9B in the operation 214. Once the endoscopic sinus surgery device 10 and the lever 14 are oriented such that the endoscopic sinus surgery device 10 is in the extended position, the surgeon can perform manual tissue resection with the surgical elevator 22 using the surgical elevator edge 24 in order to continue removing polyps during the nasal polypectomy procedure in the operation 216. Moreover, during tissue resection, the hypotube 26 of the endoscopic sinus surgery device 10 can be used to deliver irrigant 46 to the surgical site at which the polyps are being removed during the operation 218. In an example, when the irrigant 46 flows through the surgical elevator window 52, a lavage effect can be created, where the irrigant 46 goes into the surgical site and assists with washing out the surgical site during the operation 218. As one skilled in the art will appreciate, the lavage effect created by the flow of irrigant 46 to the surgical site will assist with tissue resection.

Returning to the method 200, once the operation 218 is completed, the method repeats the operation 212 to determine if further resection is needed. If further resection is not needed, the method 200 is complete.

As described above, examples of the present disclosure provide a multifunctional surgical instrument. In particular, examples of the present invention provide an endoscopic sinus surgery device that can be capable of providing manual tissue resection functionality and power tissue resection functionality. Moreover, examples of the present invention provide an endoscopic sinus surgery device that can be capable of providing irrigation during both types of tissue resection.

The above detailed description includes references to the accompanying drawings, which form a part of the detailed description. The drawings show, by way of illustration, specific examples in which the invention can be practiced. These examples are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed example. Thus, the following claims are hereby incorporated into the Detailed Description as examples or examples, with each claim standing on its own as a separate example, and it is contemplated that such examples can be combined with each other in various combinations or permutations. The scope of the invention should be determined with reference to the appended claims, along with the full scope of equivalents to which such claims are entitled.

What is claimed:

1. An endoscopic sinus surgery device comprising:
   a lever operably;
   an outer sheath operably coupled with the lever, the outer sheath including:
      a distal end;
      a proximal end;
      a surgical elevator disposed at the distal end of the outer sheath, the surgical elevator having a surgical elevator edge; and
      a hypotube extending along a length of the outer sheath to the distal end of the outer sheath, the hypotube having a hypotube access hole; and
   a shaver blade assembly, the shaver blade assembly including:
      an outer shaft partially disposed within the outer sheath;
      an outer blade disposed at a distal end of the outer shaft;
      an inner blade disposed within the outer blade, wherein the outer blade and the inner blade cooperate with each other to create a resection surface;
      a stop disposed at the distal end of the outer shaft; and
      an outer shaft access hole in a bottom surface of the outer shaft, the outer shaft access hole being proximate to the outer blade and the inner blade, wherein the lever is configured to move between a first position and a second position such that the outer sheath moves relative to the outer shaft, wherein, in the first position:
         the surgical elevator edge abuts the outer shaft stop;
         the outer shaft access hole aligns with the hypotube access hole; and
         the distal end of the outer shaft extends further than the surgical elevator edge;
      and wherein, in the second position, the surgical elevator edge is spaced apart from the outer shaft stop.

2. The endoscopic sinus surgery device of claim 1, wherein the hub assembly comprises a pathway in fluid communication with the hypotube, wherein the pathway is configured to provide irrigant to the hypotube.

3. The endoscopic sinus surgery device of claim 2, wherein, when the lever is in the first position, the shaver blade assembly is configured to provide the irrigant via the hypotube access hole and the outer shaft access hole.

4. The endoscopic sinus surgery device of claim 2, wherein a surgical elevator window is created when the surgical elevator edge is spaced apart from the outer shaft stop in the second position.

5. The endoscopic sinus surgery device of claim 4, wherein the hypotube access hole aligns with the surgical elevator window in the second position, and wherein the irrigant provided to the hypotube is provided to the surgical elevator window such that a lavage effect is created.

6. The endoscopic sinus surgery device of claim 1, wherein the lever is operably coupled with the hub assembly via upper pins such that the lever rotates about the upper pins when the lever moves between the first position and the second position.

7. The endoscopic sinus surgery device of claim 6, wherein the hub assembly further includes slots, and wherein the lever is operatively coupled with the hub assembly via lower pins disposed within the slots.

8. The endoscopic sinus surgery device of claim 7, wherein the outer sheath is operably coupled with the lever via the lower pins such that the outer sheath moves with the lever when the lever moves between the first position and the second position.

9. The endoscopic sinus surgery device of claim 1, wherein the endoscopic sinus surgery device is in a retracted position in the first position and the endoscopic sinus surgery device is in an extended position in the second position.

10. A method of operating an endoscopic sinus surgery device having a hub assembly, a lever coupled with the hub assembly, a shaver blade assembly, and an outer sheath coupled with the lever and partially disposed about the shaver blade assembly, the method comprising:
   orienting the endoscopic device in a first configuration, where the shaver blade assembly includes an outer shaft having a distal end and an outer shaft stop, where an outer blade of the shaver blade assembly is disposed at the outer shaft distal end and an inner blade is disposed within the outer blade and configured to rotate with respect to the outer blade, and the outer sheath including a surgical elevator having a surgical elevator edge where the surgical elevator edge abuts the outer shaft stop in the first configuration such that the shaver assembly is configured for tissue resection and the distal end of the outer shaft extends further than the surgical elevator edge;

providing an irrigant to the shaver blade assembly, where the outer sheath includes a hypotube having an access hole that aligns with an access hole of the outer shaft in the first configuration such that irrigant is provided to the shaver blade assembly via the hypotube access hole and the outer shaft access hole when the endoscopic sinus surgery device is in the first configuration;

orienting the endoscopic device in a second configuration, where the surgical elevator edge is spaced apart from the outer shaft stop thereby defining a surgical elevator window where the surgical elevator is configured for tissue resection and the hypotube access hole aligns with the surgical elevator window in the second configuration;

providing the irrigant to the surgical elevator window via the hypotube access hole, wherein providing the irrigant through the hypotube access hole and into the surgical elevator window creates a lavage effect.

11. The method of claim 10, wherein the hub assembly comprises a pathway in fluid communication with the hypotube, wherein the pathway is configured to provide the irrigant to the hypotube.

12. The method of claim 10, wherein the endoscopic sinus surgery device further includes a lever operably coupled with the hub assembly and the outer sheath, wherein the endoscopic sinus surgery device is oriented in the first configuration when the lever is moved to a first position and the endoscopic sinus surgery device is oriented in the second configuration when the lever is moved to a second position.

13. The method of claim 12, wherein the lever operably couples with the hub assembly via upper pins such that the lever rotates about the upper pins when the lever moves between the first position and the second position.

14. The method of claim 13, wherein the hub assembly further includes slots and the lever operatively couples with the hub assembly via lower pins disposed within the slots.

15. The method of claim 14, wherein the outer sheath operably couples with the lever via the lower pins such that the outer sheath moves with the lever when the lever moves between the first position and the second position.

16. The method of claim 10, wherein the endoscopic sinus surgery device is in a retracted position in the first configuration and the endoscopic sinus surgery device is in an extended position in the second configuration.

17. A resection assembly comprising:
a shaver blade assembly, the shaver blade assembly including:
an outer shaft comprising:
an outer blade disposed at a distal end of the outer shaft;
an inner blade disposed within the outer blade, wherein the inner blade is configured to rotate with respect to the outer blade;
a stop disposed at the distal end of the outer shaft; and
an access hole disposed at the bottom of the outer blade, the access hole being proximate to the outer blade and the inner blade;
an outer sheath partially disposed about the outer shaft and configured to move relative to the outer shaft, the outer sheath including: a surgical elevator disposed at a distal end of the outer sheath, the surgical elevator having surgical elevator edge; and
a hypotube extending along a length of the outer sheath to the distal end of the outer sheath, the hypotube having a hypotube access hole, wherein the outer sheath moves between a first position and a second position relative to the outer shaft, wherein, in the first position:
the surgical elevator edge abuts the outer shaft stop;
the outer shaft access hole aligns with the hypotube access hole; and
the distal end of the outer shaft extends further than the surgical elevator edge; and
in the second position, the surgical elevator edge is spaced apart from the outer shaft stop.

18. The resection assembly of claim 17, wherein a surgical elevator window is created when the surgical elevator edge is spaced apart from the outer shaft stop in the second position.

19. The resection assembly of claim 18, wherein the hypotube access hole aligns with the surgical elevator window in the second position.

20. The resection assembly of claim 17, wherein the resection assembly is in a retracted position in the first position and the resection assembly is in an extended position in the second position.

* * * * *

UNITED STATES PATENT AND TRADEMARK OFFICE
CERTIFICATE OF CORRECTION

PATENT NO. : 11,931,056 B2
APPLICATION NO. : 17/017936
DATED : March 19, 2024
INVENTOR(S) : Ly et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 614 days.

Signed and Sealed this
Eighth Day of October, 2024

Katherine Kelly Vidal
*Director of the United States Patent and Trademark Office*